US012655388B2

(12) United States Patent
Culshaw et al.

(10) Patent No.: US 12,655,388 B2
(45) Date of Patent: Jun. 16, 2026

(54) VIRUS-LIKE PARTICLE

(71) Applicant: AUTOLUS LIMITED, London (GB)

(72) Inventors: Abigail Culshaw, London (GB); Rosie Woodruff, London (GB); Alexander Burkard, London (GB); Martin Madill, London (GB)

(73) Assignee: AUTOLUS LIMITED, London (GB)

( * ) Notice: Subject to any disclaimer, the term of this patent is extended or adjusted under 35 U.S.C. 154(b) by 1080 days.

(21) Appl. No.: 17/626,990

(22) PCT Filed: Jul. 24, 2020

(86) PCT No.: PCT/GB2020/051777
§ 371 (c)(1),
(2) Date: Jan. 13, 2022

(87) PCT Pub. No.: WO2021/014165
PCT Pub. Date: Jan. 28, 2021

(65) Prior Publication Data
US 2022/0249566 A1      Aug. 11, 2022

(30) Foreign Application Priority Data
Jul. 25, 2019    (GB) ..................................... 1910651

(51) Int. Cl.
*A61K 35/17* (2025.01)
*A61K 40/11* (2025.01)
*A61K 40/31* (2025.01)
*A61K 40/42* (2025.01)
*C12N 5/071* (2010.01)
*C12N 5/0783* (2010.01)
*C12N 15/62* (2006.01)
*C12N 15/85* (2006.01)
*C12N 15/86* (2006.01)

(52) U.S. Cl.
CPC ............ *C12N 5/0636* (2013.01); *A61K 40/11* (2025.01); *A61K 40/31* (2025.01); *A61K 40/4211* (2025.01); *A61K 40/4212* (2025.01); *C12N 5/0638* (2013.01); *C12N 5/0687* (2013.01); *C12N 15/625* (2013.01); *C12N 15/85* (2013.01); *C12N 15/86* (2013.01); *C12N 2501/2307* (2013.01); *C12N 2501/2315* (2013.01); *C12N 2740/10022* (2013.01); *C12N 2740/10023* (2013.01); *C12N 2740/10043* (2013.01); *C12N 2800/107* (2013.01)

(58) Field of Classification Search
CPC .. C12N 5/0636; C12N 5/0638; C12N 5/0687; C12N 2501/2307; C12N 2501/2315; A61K 40/4212; A61K 40/4211; A61K 40/31; A61K 40/11
See application file for complete search history.

(56) References Cited

U.S. PATENT DOCUMENTS

| | | | |
|---|---|---|---|
| 10,745,715 B2 | 8/2020 | Pule et al. | |
| 2006/0205069 A1 | 9/2006 | June et al. | |
| 2014/0308308 A1* | 10/2014 | Anderson | ............ C07K 14/005 |
| 2015/0071987 A1 | 3/2015 | Selvaraj | |
| 2018/0311374 A1* | 11/2018 | Lobb | .................. A61K 47/6851 |
| 2019/0177746 A1 | 6/2019 | Peddareddigari et al. | |

FOREIGN PATENT DOCUMENTS

| | | |
|---|---|---|
| WO | WO-2016/030690 A1 | 3/2016 |
| WO | WO-2016/102965 A1 | 6/2016 |
| WO | WO-2016/135470 A1 | 9/2016 |
| WO | WO-2018/009923 A1 | 1/2018 |
| WO | WO-2018/033726 A1 | 2/2018 |

OTHER PUBLICATIONS

International Search Report and Written Opinion for International Application No. PCT/GB2020/051777, mailed Jan. 18, 2021, 12 Pages.
Maurice et al., "Efficient gene transfer into human primary blood lymphocytes by surface-engineered lentiviral vectors that display a T cell-activating polypeptide," Blood 99:2342-2350 (2002).
Mosca et al., "Antigen-presenting particle technology using inactivated surface-engineered viruses: induction of immune responses against infectious agents," Retrovirology 4:32, 18 pages (2007).
Paszkiet et al., "CD86 and CD54 Co-Expression on VSV-G Pseudotyped HIV-1 Based Vectors Improves Transduction and Activation of Human Primary CD4+ Lymphocytes," Blood 104(11):1754, 5 pages (2004).

* cited by examiner

*Primary Examiner* — James D Schultz
*Assistant Examiner* — Joseph Paul Miano
(74) *Attorney, Agent, or Firm* — MARSHALL, GERSTEIN & BORUN LLP

(57) ABSTRACT

The present invention provides a virus-like particle (VLP) having a viral envelope which comprises: (i) a membrane protein comprising the extracellular domain of CD86; and (ii) a CD3-binding membrane protein. The VLP may be used to activate T cells prior to viral transduction.

9 Claims, 4 Drawing Sheets
Specification includes a Sequence Listing.

aCD3 aCD28

293T cells expressing Stim proteins

VLP Production

Stim VLP
(RetroStim)

VIRUS-LIKE PARTICLE

CROSS-REFERENCE TO RELATED APPLICATIONS

This is a U.S. National Phase of International Application No. PCT/GB2020/051777, filed Jul. 24, 2020, which claims priority to Great Britain Application No. 1910651.7, filed Jul. 25, 2019.

INCORPORATION BY REFERENCE OF THE SEQUENCE LISTING

This application contains, as a separate part of disclosure, a Sequence Listing in computer-readable form (filename 55145_Seqlisting.text; 19,500 bytes-ASCII text file created Jan. 12, 2022) which is incorporated by reference herein in its entirety.

FIELD OF THE INVENTION

The present invention relates to virus-like particles (VLPs) and their use to activate cells, such as T cells.

BACKGROUND TO THE INVENTION

The generation of engineered T-cell products typically requires stimulation with a mitogen followed by transduction with an integrating vector, such as a lentiviral vector or a retroviral vector.

A widely used approach is to add soluble mitogenic monoclonal antibodies (mAb), such as anti-TCR/CD3 and anti-CD28, to the cell culture. An alternative approach is to attach anti-TCR/CD3 mAb along with anti-CD28 mAb to a bead. The surface of the bead has improved T cell activating properties compared to the soluble antibodies alone.

Mitogenic antibodies and beads are single-use consumables and typically represent the most costly part of the T-cell production process.

Maurice et al. describe the direct engineering of a lentiviral envelope protein such that the CD3 agonist OKT3 is displayed on the virion surface (Maurice et al.; Blood; 2002; 99; 2342-2350).

This engineering approach requires complex engineering of the viral envelope protein. This complex engineering must be performed for each discrete peptide to be displayed on the virion surface. The approach has also been shown to reduce viral titre.

WO2016/135470 describes including a mitogenic transmembrane protein in the producer or packaging cell, which gets incorporated into the retrovirus when it buds from the producer/packaging cell membrane. The mitogenic transmembrane protein is expressed as a separate cell surface molecule on the producer cell rather than being part of the viral envelope glycoprotein. This means that the reading frame of the viral envelope is unaffected, which therefore preserves functional integrity and viral titre.

SUMMARY OF ASPECTS OF THE INVENTION

Figure 1:
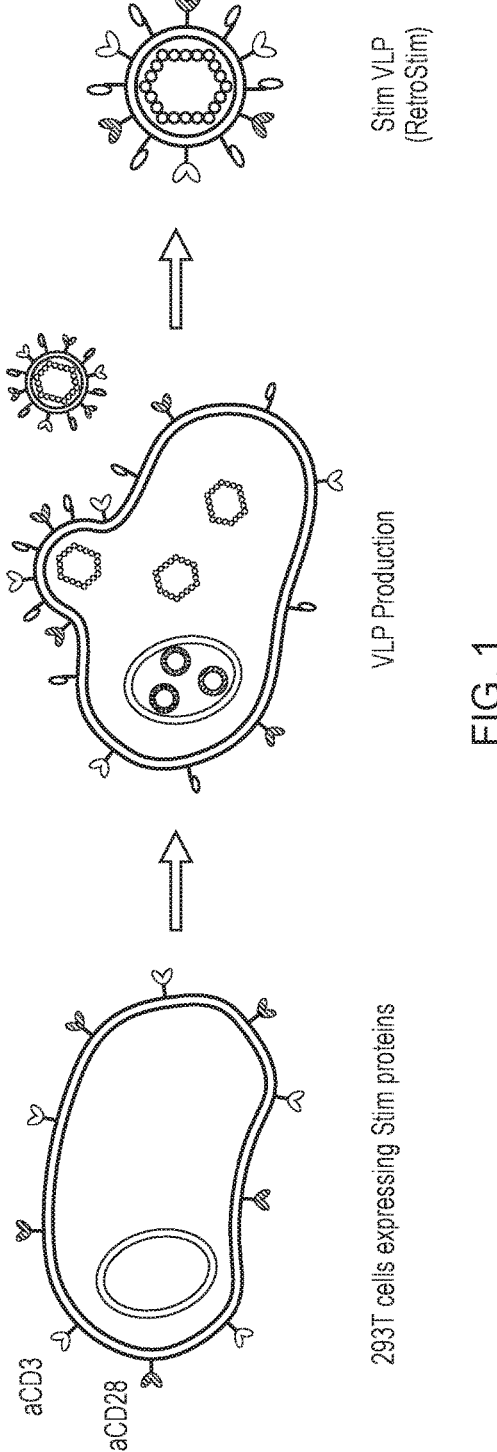
FIG. 1—Schematic diagram illustrating VLP production. Proteins expressed on VLP producer cells are passively acquired on VLP surfaces during the budding process. In the present invention, stimulatory proteins are included on the VLP surface to activate T-cells.

The present inventors have found that virus-like particles (VLPs) expressing a) a CD3-binding protein and b) a protein comprising the extracellular domain of CD86 are particularly effective for activating T cells. T cells activated by such VLPs show improved activation and expansion compared to VLPs expressing a CD3-binding transmembrane protein and a CD28-binding transmembrane protein ("RetroSTIM") as described in WO2016/135470. T cells activated by such VLPs also show a more desirable phenotype: a greater proportion of cells being naïve or central memory T cells. When such VLP-activated T cells are transduced to express a chimeric antigen receptor (CAR), the CAR-T cells show improved cytotoxicity against target cells than CAR-T cells activated using a commercially available polymeric nanomatrix conjugated to anti-CD3 anti-CD28 antibodies.

Thus, in a first aspect, the present invention provides a virus-like particle (VLP) having a viral envelope which comprises:

(i) a membrane protein comprising the extracellular domain of CD86; and (ii) a CD3-binding membrane protein.

The VLP may be derived from a retrovirus or a lentivirus. The VLP may be derived from Moloney murine leukemia virus (Mo-MLV).

The CD3-binding transmembrane protein may comprise an OKT3-derived antigen binding domain.

In a second aspect, the present invention provides a producer cell capable of producing a VLP according to the first aspect of the invention, which expresses:

(i) a membrane protein comprising the extracellular domain of CD86; and (ii) a CD3-binding membrane protein at the cell surface.

In a third aspect, the present invention provides a nucleic acid construct which comprises a first nucleic acid sequence encoding a membrane protein comprising the extracellular domain of CD86 and a second nucleic acid sequence encoding a CD3-binding transmembrane protein.

In a fourth aspect, the present invention provides a vector comprising a nucleic acid construct according to the third aspect of the invention.

In a fifth aspect, the present invention provides a kit of vectors which comprises:

(i) a first vector which comprises a nucleic acid sequence encoding a membrane protein comprising the extracellular domain of CD86; and (ii) a second vector which comprises a nucleic acid sequence encoding a CD3-binding transmembrane protein.

The kit of vectors may comprise:

a) a vector according to the fourth aspect of the invention; or b) first and second vectors according to the fifth aspect of the invention; and c) a third vector encoding Gag protein In a sixth aspect, the present invention provides a method for making a producer cell according to the second aspect of the invention which comprises the step of introducing a nucleic acid construct according to the third aspect of the invention; a vector according to the fourth aspect of the invention; or a kit of vectors according to the fifth aspect of the invention into a cell in vitro.

In a seventh aspect, there is provided a method for making a VLP according to the first aspect of the invention, which comprises the step of culturing a producer cell according to the second aspect of the invention, then harvesting VLPs from the supernatant.

In an eighth aspect, the present invention provides a method for activating a T cell which comprises the step of culturing the T cell in the presence of a VLP according to the first aspect of the invention.

The T cell may also be cultured in the presence of IL-7 or IL-15.

In a ninth aspect, the present invention provides a T cell activated by a method according to the eighth aspect of the invention.

In a tenth aspect, there is provided a method for transducing a T cell which comprises the following steps:

(i) activating a T-cell by a method according to the eighth aspect of the invention; and (ii) transducing the T cell with a viral vector.

The viral vector genome may comprise a nucleic acid sequence encoding a chimeric antigen receptor (CAR) or T-cell receptor (TCR).

In an eleventh aspect, the invention provides a CAR- or TCR-expressing T cell made by a method according to the tenth aspect of the invention.

In a twelfth aspect, the present invention provides a composition of cells according to the ninth or eleventh aspect of the invention.

In a thirteenth aspect, there is provided a method for treating a disease in a subject which comprises the step of administering a cell composition according to the twelfth aspect of the invention to the subject.

In a fourteenth aspect, the present invention provides a cell composition according to the twelfth aspect of the invention for use in treating and/or preventing a disease.

In a fifteenth aspect, there is provided the use of a cell composition according to the twelfth aspect of the invention in the manufacture of a medicament for treating and/or preventing a disease.

The disease may be cancer.

DETAILED DESCRIPTION

The present invention relates to virus-like particles (VLPs) which may be derived from a retrovirus or lentivirus.

Retroviruses

Retroviruses are double stranded RNA enveloped viruses mainly characterized by the ability to "reverse-transcribe" their genome from RNA to DNA. Virions measure 100-120 nm in diameter and contain a dimeric genome of identical positive RNA strands complexed with the nucleocapsid proteins. The genome is enclosed in a protein capsid that also contains enzymatic proteins, namely the reverse transcriptase, the integrase and proteases, required for viral infection. The matrix proteins form a layer outside the capsid core that interacts with the envelope, a lipid bilayer derived from the host cellular membrane, which surrounds the viral core particle. Anchored on this bilayer, are the viral envelope glycoproteins responsible for recognizing specific receptors on the host cell and initiating the infection process. Envelope proteins are formed by two subunits, the transmembrane (TM) that anchors the protein into the lipid membrane and the surface (SU) which binds to the cellular receptors.

Based on the genome structure, retroviruses are classified into simple retroviruses, such as MLV and murine leukemia virus; or complex retroviruses, such as HIV and EIAV. Retroviruses encode four genes: gag (group specific antigen), pro (protease), pol (polymerase) and env (envelope). The gag sequence encodes the three main structural proteins: the matrix protein, nucleocapsid proteins, and capsid protein. The pro sequence encodes proteases responsible for cleaving Gag and Gag-Pol during particle assembly, budding and maturation. The pol sequence encodes the enzymes reverse transcriptase and integrase, the former catalyzing the reverse transcription of the viral genome from RNA to DNA during the infection process and the latter responsible for integrating the proviral DNA into the host cell genome. The env sequence encodes for both SU and TM subunits of the envelope glycoprotein. Additionally, retroviral genome presents non-coding cis-acting sequences such as: two LTRs (long terminal repeats), which contain elements required to drive gene expression, reverse transcription and integration into the host cell chromosome; a sequence named packaging signal ($\psi$) required for specific packaging of the viral RNA into newly forming virions; and a polypurine tract (PPT) that functions as the site for initiating the positive strand DNA synthesis during reverse transcription. In addition to gag, pro, pol and env, complex retroviruses, such as lentiviruses, have accessory genes including vif, vpr, vpu, nef, tat and rev that regulate viral gene expression, assembly of infectious particles and modulate viral replication in infected cells.

During the process of infection, a retrovirus initially attaches to a specific cell surface receptor. On entry into the susceptible host cell, the retroviral RNA genome is then copied to DNA by the virally encoded reverse transcriptase which is carried inside the parent virus. This DNA is transported to the host cell nucleus where it subsequently integrates into the host genome. At this stage, it is typically referred to as the provirus. The provirus is stable in the host chromosome during cell division and is transcribed like other cellular proteins. The provirus encodes the proteins and packaging machinery required to make more virus, which can leave the cell by a process known as "budding".

When enveloped viruses, such as retrovirus and lentivirus, bud out of the host cells, they take part of the host cell lipidic membrane. In this way, host-cell derived membrane proteins become part of the retroviral particle. The present invention utilises this process in order to introduce proteins of interest into the envelope of a virus-like particle.

Retroviral Vectors

Retroviruses and lentiviruses may be used as a vector or delivery system for the transfer of a gene to a target cell. The transfer can occur in vitro, ex vivo or in vivo. When used in this fashion, the viruses are typically called viral vectors.

Gamma-retroviral vectors, commonly designated retroviral vectors, were the first viral vector employed in gene therapy clinical trials in 1990 and are still one of the most used. More recently, the interest in lentiviral vectors, derived from complex retroviruses such as the human immunodeficiency virus (HIV), has grown due to their ability to transduce non-dividing cells. The most attractive features of retroviral and lentiviral vectors as gene transfer tools include the capacity for large genetic payload (up to 9 kb), minimal patient immune response, high transducing efficiency in vivo and in vitro, and the ability to permanently modify the genetic content of the target cell, sustaining a long-term expression of the delivered gene.

Virus-Like Particles (VLPs)

For retroviral and lentiviral vectors, the expression of the Gag precursor is sufficient to mediate virion assembly and release. Gag proteins, and even fragments of Gag, have been shown competent to assemble in vitro to form various structures that resemble virion cores. These particles that are devoid of viral genetic material, and are hence non-infectious, are called virus-like particles (VLPs). Like with complete viral particles they contain an outer viral envelope made of the host cell lipid-bi-layer (membrane), and hence contain host cell transmembrane proteins (see FIG. 1).

The VLP of the present invention can be based on or derivable from any suitable virus which an outer viral envelope made of the host cell membrane. For example, the VLP may be based on an alpharetrovirus, a gammaretrovirus, or a spumaretrovirus.

The VLP may be derived from a gammaretrovirus, such as a Murine Leukemia Virus (MLV). The MLV may be derived from Moloney Murine Leukemia Virus (MMLV)

The VLP of the present invention may be based on or derivable from a lentivirus. The VLP may be based on a non-primate lentivirus such as equine infectious anemia virus (EIAV). The VLP may alternatively be based on human immunodeficiency virus (HIV).

Host Cell

In a second aspect, the invention provides a host cell which expresses (i) a membrane protein comprising the extracellular domain of CD86 and (ii) a CD3-binding membrane protein at the cell surface.

The host cell may be for the production of VLPs according to the first aspect of the invention.

The host cell may be a producer cell and comprise a gag, and optionally a pol gene(s).

The host cell lacks a retroviral or lentiviral vector genome.

The host-cell may be made by transient transfection with one or more plasmids encoding (i) a membrane protein comprising the extracellular domain of CD86 and (ii) a CD3-binding membrane protein, and optionally a plasmid encoding Gag and optionally Pol. Alternatively the host cell may stably express (i) a membrane protein comprising the extracellular domain of CD86 and (ii) a CD3-binding membrane protein. The host cell may stably express (i) a membrane protein comprising the extracellular domain of CD86, (ii) a CD3-binding membrane protein, (iii) Gag and optionally Pol.

The host cell may be a human cell, such as a HEK 293T cell.

CD3-Binding Membrane Protein

The VLP of the present invention comprise mitogenic T-cell activating membrane proteins in the viral envelope. The mitogenic T-cell activating membrane proteins are made by the producer cell and expressed at the cell surface. When the nascent VLP buds from the host cell membrane, the mitogenic T-cell activating membrane proteins are incorporated in the viral envelope as part of the producer cell-derived lipid bilayer.

The first mitogenic T-cell activating membrane protein binds to CD3. It may, for example, comprise a CD3-binding domain derived from an anti-CD3 antibody.

CD3 is a T-cell co-receptor. It is a protein complex composed of four distinct chains. In mammals, the complex contains a CD3γ chain, a CD3δ chain, and two CD3ε chains. These chains associate with the T-cell receptor (TCR) and the ζ-chain to generate an activation signal in T lymphocytes. The TCR, ζ-chain, and CD3 molecules together comprise the TCR complex.

The mitogenic domain may bind to CD3 ε chain.

Various anti-CD3 antibodies are known, including OKT3, UCHT1, YTH12.5 and TR66

OKT3, also known as Muromonab-CD3 is a monoclonal antibody targeted at the CD3ε chain. It is clinically used to reduce acute rejection in patients with organ transplants. It was the first monoclonal antibody to be approved for clinical use in humans. The CDRs of OKT3 are as follows:

```
                                      (SEQ ID No. 1)
         CDRH1:             GYTFTRY (SEQ ID No. 2)
         CDRH2:             NPSRGY (SEQ ID No. 3)
         CDRH3:             YYDDHYCLDY (SEQ ID No. 4)
         CDRL1:             SASSSVSYMN (SEQ ID No. 5)
         CDRL2:             DTSKLAS (SEQ ID No. 6)
         CDRL3:             QQWSSNPFT
```

The CD3-binding transmembrane protein may comprise the CDRs of OKT3 shown as SEQ ID No. 1-6 above. The CD3-binding transmembrane protein may comprise the VH and/or VL domains of OKT3 or the scFv of OKT3 shown below as SEQ ID No. 7.

```
(OKT3 scFv)
                                       SEQ ID No. 7
METDTLLLWVLLLWVPGSTGQVQLQQSGAELARPGASVKMSCKASGYTF

TRYTMHWVKQRPGQGLEWIGYINPSRGYTNYNQKFKDKATLTTDKSSST

AYMQLSSLTSEDSAVYYCARYYDDHYCLDYWGQGTTLTVSSSGGGGSGG

GGSGGGGSQIVLTQSPAIMSASPGEKVTMTCSASSSVSYMNWYQQKSGT

SPKRWIYDTSKLASGVPAHFRGSGSGTSYSLTISGMEAEDAATYYCQQW

SSNPFTFGSGTKLEINRSDP
```

The CD3-binding membrane protein may comprise a variant of the sequence shown as SEQ ID No. 7 having at least 80, 85, 90, 95, 98 or 99% sequence identity, provided that the variant sequence binds CD3.

The CD3-binding transmembrane protein may have the structure:

aCD3-S-TM in which aCD3 is CD3-binding domain; S is an optional spacer domain and TM is a transmembrane domain.

Membrane Protein Comprising the Extracellular Domain of CD86

The second mitogenic T-cell activating membrane protein comprises the extracellular domain of CD86.

Cluster of Differentiation 86 (also known as CD86 and B7-2) is a protein expressed on antigen-presenting cells that provides costimulatory signals necessary for T cell activation and survival. It is the ligand for two different proteins on the T cell surface: CD28 (for autoregulation and intercellular association) and CTLA-4 (for attenuation of regulation and cellular disassociation). CD86 works in tandem with CD80 to prime T cells.

The CD86 gene encodes a type I membrane protein that is a member of the immunoglobulin superfamily. The full sequence for human CD86 is available for Uniprot, Accession number P42081. CD86 is a 329 amino acid sequence, of which amino acids 1-23 are the signal peptide; 24-247 are the extracellular domain; 248-268 are the transmembrane domain and 269-329 are the cytoplasmic domain.

The amino acid sequence of the extracellular domain of human CD86, including the signal peptide, is shown below as SEQ ID No. 8.

```
                                  SEQ ID No. 8
DPQCTMGLSNILFVMAFLLSGAAPLKIQAYFNETADLPCQFANSQNQS

LSELVVFWQDQENLVLNEVYLGKEKFDSVHSKYMGRTSFDSDSWTLRL

HNLQIKDKGLYQCIIHHKKPTGMIRIHQMNSELSVLANFSQPEIVPIS

NITENVYINLTCSSIHGYPEPKKMSVLLRTKNSTIEYDGVMQKSQDNV

TELYDVSISLSVSFPDVTSNMTIFCILETDKTRLLSSPFSIELEDPQP

PPDHIP
```

The second mitogenic T-cell activating membrane protein may comprise the sequence shown as SEQ ID No. 8 or a variant thereof. The variant sequence may have 70%, 80%, 90%, 95% or 99% identity to the sequence shown as SEQ ID No. 8, as long as it retains the capacity to bind CD28 and activate T cells.

Spacer Domain

The first and/or second mitogenic T-cell activating membrane protein(s) may comprise a spacer sequence to connect the CD3-binding domain or CD86 extracellular domain with the membrane targeting domain. A flexible spacer allows the CD3-binding domain or CD86 extracellular domain to orient in different directions to facilitate binding.

The spacer sequence may, for example, comprise an IgG1 Fc region, an IgG1 hinge or a human CD8 stalk or the mouse CD8 stalk. The spacer may alternatively comprise an alternative linker sequence which has similar length and/or domain spacing properties as an IgG1 Fc region, an IgG1 hinge or a CD8 stalk. A human IgG1 spacer may be altered to remove Fc binding motifs.

Examples of amino acid sequences for these spacers are given below:

```
(hinge-CH2CH3 of human IgG1)
                                  SEQ ID No. 9
AEPKSPDKTHTCPPCPAPPVAGPSVFLFPPKPKDTLMIARTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ
```

```
                                          -continued
VSLTCLVKGFYPSDIAVEWESNGQPENNYKTTPPVLDSDGSFFLYSKLT

VDKSRWQQGNVFSCSVMHEALHNHYTQKSLSLSPGKKD (human CD8 stalk):
                                  SEQ ID No. 10
TTTPAPRPPTPAPTIASQPLSLRPEACRPAAGGAVHTRGLDFACDI (human IgG1 hinge):
                                  SEQ ID No. 11
AEPKSPDKTHTCPPCPKDPK (CD2 ecto domain)
                                  SEQ ID No. 12
KEITNALETWGALGQDINLDIPSFQMSDDIDDIKWEKTSDKKKIAQFRK

EKETFKEKDTYKLFKNGTLKIKHLKTDDQDIYKVSIYDTKGKNVLEKIF

DLKIQERVSKPKISWTCINTTLTCEVMNGTDPELNLYQDGKHLKLSQRV

ITHKWTTSLSAKFKCTAGNKVSKESSVEPVSCPEKGLD (CD34 ecto domain)
                                  SEQ ID No. 13
SLDNNGTATPELPTQGTFSNVSTNVSYQETTTPSTLGSTSLHPVSQHGN

EATTNITETTVKFTSTSVITSVYGNTNSSVQSQTSVISTVFTTPANVST

PETTLKPSLSPGNVSDLSTTSTSLATSPTKPYTSSSPILSDIKAEIKCS

GIREVKLTQGICLEQNKTSSCAEFKKDRGEGLARVLCGEEQADADAGAQ

VCSLLLAQSEVRPQCLLLVLANRTEISSKLQLMKKHQSDLKKLGILDFT

EQDVASHQSYSQKT
```

Membrane Targeting Domain

The term "membrane protein" as used herein indicates that the protein is located at the membrane of the VLP. The CD3-binding domain and extracellular domain of CD86 are located on the outside of the VLP membrane. The first and second mitogenic T-cell activating membrane proteins comprise a membrane targeting domain, which is a sequence which causes the protein to be localised to the membrane.

The membrane localisation domain may, for example, comprise a transmembrane sequence, a stop transfer sequence, a GPI anchor or a myristoylation/prenylation/palmitoylation site.

A transmembrane domain is a portion of sequence which spans the membrane. The transmembrane domain may comprise a hydrophobic alpha helix. The transmembrane domain may be derived from CD8.

An alternative option to a transmembrane domain is a membrane-targeting domain such as a GPI anchor.

GPI anchoring is a post-translational modification which occurs in the endoplasmic reticulum. Preassembled GPI anchor precursors are transferred to proteins bearing a C-terminal GPI signal sequence. During processing, the GPI anchor replaces the GPI signal sequence and is linked to the target protein via an amide bond. The GPI anchor targets the mature protein to the membrane.

Myristoylation is a lipidation modification where a myristoyl group, derived from myristic acid, is covalently attached by an amide bond to the alpha-amino group of an N-terminal glycine residue. Myristic acid is a 14-carbon saturated fatty acid also known as n-Tetradecanoic acid. The modification can be added either co-translationally or post-translationally. N-myristoyltransferase (NMT) catalyzes the myristic acid addition reaction in the cytoplasm of cells. Myristoylation causes membrane targeting of the protein to which it is attached, as the hydrophobic myristoyl group interacts with the phospholipids in the cell membrane.

The mitogenic T-cell activating protein may comprise a sequence capable of being myristoylated by a NMT enzyme. The mitogenic T-cell activating protein may comprise a myristoyl group when expressed in a cell.

The mitogenic T-cell activating protein may comprise a consensus sequence such as: NH2-G1-X2-X3-X4-S5-X6-X7-X8 which is recognised by NMT enzymes.

Palmitoylation is the covalent attachment of fatty acids, such as palmitic acid, to cysteine and less frequently to serine and threonine residues of proteins. Palmitoylation enhances the hydrophobicity of proteins and can be used to induce membrane association. In contrast to prenylation and myristoylation, palmitoylation is usually reversible (because the bond between palmitic acid and protein is often a thioester bond). The reverse reaction is catalysed by palmitoyl protein thioesterases.

In signal transduction via G protein, palmitoylation of the α subunit, prenylation of the γ subunit, and myristoylation is involved in tethering the G protein to the inner surface of the plasma membrane so that the G protein can interact with its receptor.

The mitogenic T-cell activating protein may comprise a sequence capable of being palmitoylated. The mitogenic T-cell activating protein may comprise additional fatty acids when expressed in a cell which causes membrane localisation.

Prenylation (also known as isoprenylation or lipidation) is the addition of hydrophobic molecules to a protein or chemical compound. Prenyl groups (3-methyl-but-2-en-1-yl) facilitate attachment to cell membranes, similar to lipid anchors like the GPI anchor.

Protein prenylation involves the transfer of either a farnesyl or a geranyl-geranyl moiety to C-terminal cysteine(s) of the target protein. There are three enzymes that carry out prenylation in the cell, farnesyl transferase, Caax protease and geranylgeranyl transferase I.

The mitogenic T-cell activating protein may comprise a sequence capable of being prenylated. The mitogenic T-cell activating protein may comprise one or more prenyl groups when expressed in a cell which causes membrane localisation.

The mitogenic T-cell activating protein may comprise the CD8 stalk and/or transmembrane domain.

The CD3-binding membrane protein may comprise the sequence shown as SEQ ID No. 14 which is make up of an OKT3 scFv sequence and the CD8 stalk and transmembrane sequence.

```
(OKT3-CD8STK-TM-A)
                                   SEQ ID No. 14
METDTLLLWVLLLWVPGSTGQVQLQQSGAELARPGASVKMSCKASGYTF

TRYTMHWVKQRPGQGLEWIGYINPSRGYTNYNQKFKDKATLTTDKSSST

AYMQLSSLTSEDSAVYYCARYYDDHYCLDYWGQGTTLTVSSSGGGGSGG

GGSGGGGSQIVLTQSPAIMSASPGEKVTMTCSASSSVSYMNWYQQKSGT

SPKRWIYDTSKLASGVPAHFRGSGSGTSYSLTISGMEAEDAATYYCQQW

SSNPFTFGSGTKLEINRSDPTTTPAPRPPTPAPTIASQPLSLRPEACRP

AAGGAVHTRGLDFACDIYIWAPLAGTCGVLLLSLVITLYCNHRNRRRVC

KCPRPVV
```

The membrane protein comprising the extracellular domain of CD86 may comprise the sequence shown as SEQ ID No. 15 which is made up of the extracellular domain of CD86 and the CD8 transmembrane domain.

```
(CD86-CD8TM)
                                   SEQ ID No. 15
DPQCTMGLSNILFVMAFLLSGAAPLKIQAYFNETADLPCQFANSQNQSL

SELVVFWQDQENLVLNEVYLGKEKFDSVHSKYMGRTSFDSDSWTLRLHN

LQIKDKGLYQCIIHHKKPTGMIRIHQMNSELSVLANFSQPEIVPISNIT

ENVYINLTCSSIHGYPEPKKMSVLLRTKNSTIEYDGVMQKSQDNVTELY

DVSISLSVSFPDVTSNMTIFCILETDKTRLLSSPFSIELEDPQPPPDHI

PIYIWAPLAGTCGVLLLSLVITLYCNHRNRRRVCKCPRPVVNAYVATAD

MYRARAGSIPPPP
```

The mitogenic T-cell activating protein may comprise a variant of the sequence shown as SEQ ID No. 14 or 15 having at least 80, 85, 90, 95, 98 or 99% sequence identity, provided that the variant sequence is a mitogenic T-cell activating protein having the required properties i.e. the capacity to bind CD3 or CD28 and activate a T cell when present in the envelope of a VLP.

Methods of sequence alignment are well known in the art and are accomplished using suitable alignment programs. The % sequence identity refers to the percentage of amino acid or nucleotide residues that are identical in the two sequences when they are optimally aligned. Nucleotide and protein sequence homology or identity may be determined using standard algorithms such as a BLAST program (Basic Local Alignment Search Tool at the National Center for Biotechnology Information) using default parameters, which is publicly available at http://blast.ncbi.nlm.nih.gov. Other algorithms for determining sequence identity or homology include: LALIGN (www.ebi.ac.uk/Tools/psa/lalign/and www.ebi.ac.uk/Tools/psa/lalign/nucleotide.html), AMAS (Analysis of Multiply Aligned Sequences, at www.compbio.dundee.ac.uk/Software/Amas/amas.html), FASTA (www.ebi.ac.uk/Tools/sss/fasta/), Clustal Omega (www.ebi.ac.uk/Tools/msa/clustalo/), SIM (web.expasy.org/sim/), and EMBOSS Needle (www.ebi.ac.uk/Tools/psa/emboss_needle/nucleotide.html).

Nucleic Acid

The invention also relates to a nucleic acid encoding a CD3-binding transmembrane protein or a nucleic acid encoding a membrane protein comprising the extracellular domain of CD86. The nucleic acid may be in the form of a construct comprising a plurality of sequences one encoding a CD3-binding transmembrane protein and one encoding a membrane protein comprising the extracellular domain of CD86.

As used herein, the terms "polynucleotide", "nucleotide", and "nucleic acid" are intended to be synonymous with each other.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

Nucleic acids may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the use as described herein, it is to be understood that the polynucleotides may be modified by any method available in the art. Such modifications may be carried out in order to enhance the in vivo activity or life span of polynucleotides of interest.

The terms "variant", "homologue" or "derivative" in relation to a nucleotide sequence include any substitution of, variation of, modification of, replacement of, deletion of or addition of one (or more) nucleic acid from or to the sequence.

The nucleic acid may produce a polypeptide which comprises one or more sequences encoding a CD3-binding transmembrane protein and/or one or more sequences encoding a membrane protein comprising the extracellular domain of CD86. The cleavage site may be self-cleaving, such that when the polypeptide is produced, it is immediately cleaved into the receptor component and the signalling component without the need for any external cleavage activity.

Various self-cleaving sites are known, including the Foot-and-Mouth disease virus (FMDV) 2a self-cleaving peptide and various variants and 2A-like peptides. The peptide may have the sequence shown as SEQ ID No. 16 or 17.

```
                                        SEQ ID No. 16
        RAEGRGSLLTCGDVEENPGP.

SEQ ID No 17
        QCTNYALLKLAGDVESNPGP
```

The co-expressing sequence may be an internal ribosome entry sequence (IRES). The co-expressing sequence may be an internal promoter.

Vector

The present invention also provides a vector, or kit of vectors which comprises a sequence encoding a CD3-binding transmembrane protein and/or a sequence encoding a membrane protein comprising the extracellular domain of CD86. Such a vector may be used to introduce the nucleic acid sequence(s) into a host cell, such as a producer or packaging cell.

The vector may, for example, be a plasmid.

Alternatively the vector may be a viral vector, such as a retroviral vector or a lentiviral vector.

The vector may be capable of transfecting or transducing a host cell.

A kit of vectors may also comprise vector(s) encoding gag and/or pol proteins.

Methods

The invention also provides a method for activating a cell which comprises the step of culturing the cell in the presence of a VLP of the invention.

The cell may be a cytolytic immune cell such as a T cell or NK cell. The method of activation may take 48 hours or less, for example between 24 and 48 hours.

The invention also provides a method for transducing a cell which comprises the following steps:

(i) activating a cell as described above; and (ii) transducing the cell with a viral vector.

The viral vector genome may comprise a nucleic acid sequence encoding a chimeric antigen receptor (CAR) or T-cell receptor (TCR).

Chimeric Antigen Receptors (CARs)

CARs are chimeric type I trans-membrane proteins which connect an extracellular antigen-recognizing domain (binder) to an intracellular signalling domain (endodomain). The binder is typically a single-chain variable fragment (scFv) derived from a monoclonal antibody (mAb), but it can be based on other formats which comprise an antibody-like antigen binding site. A spacer domain is usually necessary to isolate the binder from the membrane and to allow it a suitable orientation. A common spacer domain used is the Fc of IgG1. More compact spacers can suffice e.g. the stalk from CD8a and even just the IgG1 hinge alone, depending on the antigen. A trans-membrane domain anchors the protein in the cell membrane and connects the spacer to the endodomain.

Early CAR designs had endodomains derived from the intracellular parts of either the γ chain of the FcεR1 or CD3ζ. Consequently, these first generation receptors transmitted immunological signal 1, which was sufficient to trigger T-cell killing of cognate target cells but failed to fully activate the T-cell to proliferate and survive. To overcome this limitation, compound endodomains have been constructed: fusion of the intracellular part of a T-cell co-stimulatory molecule to that of CD3ζ results in second generation receptors which can transmit an activating and co-stimulatory signal simultaneously after antigen recognition. The co-stimulatory domain most commonly used is that of CD28. This supplies the most potent co-stimulatory signal—namely immunological signal 2, which triggers T-cell proliferation. Some receptors have also been described which include TNF receptor family endodomains, such as the closely related OX40 and 41BB which transmit survival signals. Even more potent third generation CARs have now been described which have endodomains capable of transmitting activation, proliferation and survival signals.

CAR-encoding nucleic acids may be transferred to T cells using, for example, retroviral or lentiviral vectors to generate cancer-specific T cells for adoptive cell transfer. When the CAR binds the target-antigen, this results in the transmission of an activating signal to the T-cell it is expressed on. Thus, the CAR directs the specificity and cytotoxicity of the T cell towards tumour cells expressing the targeted antigen.

The antigen-binding domain of the CAR may bind a tumour associated antigen. Various tumour associated antigens (TAA) are known, for example as shown in the following Table 1.

TABLE 1

| Cancer type | TAA |
| --- | --- |
| Diffuse Large B-cell Lymphoma | CD19, CD20, CD22 |
| Breast cancer | ErbB2, MUC1 |
| AML | CD13, CD33 |
| Neuroblastoma | GD2, NCAM, ALK, GD2 |
| B-CLL | CD19, CD52, CD160 |
| Colorectal cancer | Folate binding protein, CA-125 |
| Chronic Lymphocytic Leukaemia | CD5, CD19 |
| Glioma | EGFR, Vimentin |
| Multiple myeloma | BCMA, CD138 |
| Renal Cell Carcinoma | Carbonic anhydrase IX, G250 |
| Prostate cancer | PSMA |
| Bowel cancer | A33 |

A CAR may have the general formula:

Signal peptide—antigen binding domain—spacer domain—transmembrane domain—intracellular T cell signaling domain (endodomain).

The CAR may comprise a spacer sequence to connect the antigen binding domain with the transmembrane domain and spatially separate the antigen binding domain from the endodomain. A flexible spacer allows to the antigen binding domain to orient in different directions to enable antigen binding.

The spacer sequence may, for example, comprise an IgG1 Fc region, an IgG1 hinge or a CD8 stalk, or a combination thereof. The spacer may alternatively comprise an alternative sequence which has similar length and/or domain spacing properties as an IgG1 Fc region, an IgG1 hinge or a CD8 stalk.

The CAR may comprise or associate with an activating endodomain: the signal-transmission portion of the CAR. After antigen recognition, receptors cluster and a signal is transmitted to the cell. The most commonly used endodomain component is that of CD3-zeta which contains 3 ITAMs. This transmits an activation signal to the T cell after antigen is bound. CD3-zeta may not provide a fully competent activation signal and additional co-stimulatory signaling may be needed. For example, the endodomains from CD28, 4-1BB or OX40 can be used with CD3-Zeta to transmit a proliferative/survival signal, or three can be used together, e.g. OX-40/CD28/CD3z or 4-1BB/CD28/CD3z. A costimulatory signaling region may be or comprise the signaling region of CD28, OX-40, 4 IBB, CD27, inducible T cell costimulator (ICOS), CD3 gamma, CD3 delta, CD3 epsilon, CD247, Ig alpha (CD79a), or Fc gamma receptor.

The endodomain may comprise:

(i) an ITAM-containing endodomain, such as the endodomain from CD3 zeta; and/or (ii) a co-stimulatory domain, such as the endodomain from CD28; and/or (iii) a domain which transmits a survival signal, for example a TNF receptor family endodomain such as OX-40 or 4-1BB.

Transgenic T-Cell Receptor

The T-cell receptor (TCR) is a molecule found on the surface of T cells which is responsible for recognizing fragments of antigen as peptides bound to major histocompatibility complex (MHC) molecules.

The TCR is a heterodimer composed of two different protein chains. In humans, in 95% of T cells the TCR consists of an alpha (α) chain and a beta (β) chain (encoded by TRA and TRB, respectively), whereas in 5% of T cells the TCR consists of gamma and delta (γ/δ) chains (encoded by TRG and TRD, respectively).

When the TCR engages with antigenic peptide and MHC (peptide/MHC), the T lymphocyte is activated through signal transduction.

In contrast to conventional antibody-directed target antigens, antigens recognized by the TCR can include the entire array of potential intracellular proteins, which are processed and delivered to the cell surface as a peptide/MHC complex.

It is possible to engineer cells to express heterologous (i.e. non-native) TCR molecules by artificially introducing the TRA and TRB genes; or TRG and TRD genes into the cell using vectors. For example, the genes for engineered TCRs may be reintroduced into autologous T cells and transferred back into patients for T cell adoptive therapies. Such 'heterologous' TCRs may also be referred to herein as 'transgenic TCRs'.

Cell Composition

The present invention also provides a composition of cells activated by the method of the invention. The cell composition may comprise CAR- or TCR-expressing cells.

The cell composition may comprise cytolytic immune cells such as a T cells and/or or NK cells.

T cells or T lymphocytes are a type of lymphocyte that play a central role in cell-mediated immunity. They can be distinguished from other lymphocytes, such as B cells and natural killer cells (NK cells), by the presence of a T-cell receptor (TCR) on the cell surface. There are various types of T cell, as summarised below.

Helper T helper cells (TH cells) assist other white blood cells in immunologic processes, including maturation of B cells into plasma cells and memory B cells, and activation of cytotoxic T cells and macrophages. TH cells express CD4 on their surface. TH cells become activated when they are presented with peptide antigens by MHC class II molecules on the surface of antigen presenting cells (APCs). These cells can differentiate into one of several subtypes, including TH1, TH2, TH3, TH17, Th9, or TFH, which secrete different cytokines to facilitate different types of immune responses.

Cytolytic T cells (TC cells, or CTLs) destroy virally infected cells and tumor cells, and are also implicated in transplant rejection. CTLs express the CD8 at their surface. These cells recognize their targets by binding to antigen associated with MHC class I, which is present on the surface of all nucleated cells. Through IL-10, adenosine and other molecules secreted by regulatory T cells, the CD8+ cells can be inactivated to an anergic state, which prevent autoimmune diseases such as experimental autoimmune encephalomyelitis.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells (TCM cells) and two types of effector memory T cells (TEM cells and TEMRA cells). Memory cells may be either CD4+ or CD8+. Memory T cells typically express the cell surface protein CD45RO.

Regulatory T cells (Treg cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of CD4+ Treg cells have been described—naturally occurring Treg cells and adaptive Treg cells.

Naturally occurring Treg cells (also known as CD4+CD25+FoxP3+ Treg cells) arise in the thymus and have been linked to interactions between developing T cells with both myeloid (CD11c+) and plasmacytoid (CD123+) dendritic cells that have been activated with TSLP. Naturally occurring Treg cells can be distinguished from other T cells by the presence of an intracellular molecule called FoxP3. Mutations of the FOXP3 gene can prevent regulatory T cell development, causing the fatal autoimmune disease IPEX.

Adaptive Treg cells (also known as Tr1 cells or Th3 cells) may originate during a normal immune response.

Natural Killer cells (or NK cells) form part of the innate immune system. NK cells provide rapid responses to innate signals from virally infected cells in an MHC independent manner.

NK cells (belonging to the group of innate lymphoid cells) are defined as large granular lymphocytes (LGL) and constitute the third kind of cells differentiated from the common lymphoid progenitor generating B and T lymphocytes. NK cells are known to differentiate and mature in the bone marrow, lymph node, spleen, tonsils and thymus where they then enter into the circulation.

The cells of the invention may be any of the cell types mentioned above.

The cells to be activated by the method of the invention may be derived from a blood sample, for example from a leukapheresate. The cells may be or comprise peripheral blood mononuclear cells (PBMCs).

Cells may either be created ex vivo either from a patient's own peripheral blood (1st party), or in the setting of a haematopoietic stem cell transplant from donor peripheral blood (2nd party), or peripheral blood from an unconnected donor (3rd party).

Alternatively, cells may be derived from ex vivo differentiation of inducible progenitor cells or embryonic progenitor cells to, for example, T or NK cells. Alternatively, an immortalized T-cell line which retains its lytic function and could act as a therapeutic may be used.

The composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

Method of Treatment

The present invention provides a method for treating a disease which comprises the step of administering a cell composition of the present invention (for example in a pharmaceutical composition as described above) to a subject.

A method for treating a disease relates to the therapeutic use of the cell composition of the present invention. The cell composition may be administered to a subject having an existing disease or condition in order to lessen, reduce or improve at least one symptom associated with the disease and/or to slow down, reduce or block the progression of the disease.

The method for preventing a disease relates to the prophylactic use of the cell composition of the present invention. The cell composition may be administered to a subject who has not yet contracted the disease and/or who is not showing any symptoms of the disease to prevent or impair the cause of the disease or to reduce or prevent development of at least one symptom associated with the disease. The subject may have a predisposition for, or be thought to be at risk of developing, the disease.

The method may involve the steps of:

(i) isolating a cell-containing sample;
(ii) activating the cells using a method of the invention
(iii) transducing the such cells;
(iv) administering the cells from (iii) to a subject.

The present invention also provides a cell composition of the present invention for use in treating and/or preventing a disease.

The invention also relates to the use of a cell composition of the present invention in the manufacture of a medicament for the treatment of a disease.

The disease to be treated by the methods of the present invention may be a cancerous disease, such as bladder cancer, breast cancer, colon cancer, endometrial cancer, kidney cancer (renal cell), leukaemia, lung cancer, melanoma, non-Hodgkin lymphoma, pancreatic cancer, prostate cancer and thyroid cancer.

The disease may be Multiple Myeloma (MM), B-cell Acute Lymphoblastic Leukaemia (B-ALL), Chronic Lymphocytic Leukaemia (CLL), Neuroblastoma, T-cell acute Lymphoblastic Leukaema (T-ALL) or diffuse large B-cell lymphoma (DLBCL).

The disease may be a plasma cell disorder such as plasmacytoma, plasma cell leukemia, multiple myeloma, macroglobulinemia, amyloidosis, Waldenstrom's macroglobulinemia, solitary bone plasmacytoma, extramedullary plasmacytoma, osteosclerotic myeloma, heavy chain diseases, monoclonal gammopathy of undetermined significance or smoldering multiple myeloma.

The cells of the composition of the present invention may be capable of killing target cells, such as cancer cells. The target cell may be characterised by the presence of a soluble ligand together with the expression of a tumour-associated antigen (TAA) at the target cell surface.

The invention will now be further described by way of Examples, which are meant to serve to assist one of ordinary skill in the art in carrying out the invention and are not intended in any way to limit the scope of the invention.

EXAMPLES

Example 1—Production of Virus-Like Particles

To generate VLPs, HEK293T cells were seeded into flasks and cultured overnight. After 24 hours, cells were transfected with two plasmids: one encoding Gag-Pol proteins and one encoding one of the following combinations of proteins:

aCD3-aCD28: a CD3-binding transmembrane protein and a CD28-binding transmembrane protein ("RetroSTIM"); or aCD3-CD86: a CD3-binding transmembrane protein and a membrane protein comprising the extracellular domain of CD86.

The aCD3 protein is OKT3-CD8STK-TM-A, having the sequence shown above as SEQ ID No. 14. The aCD28 protein is described in WO2016/135470 and is 15E8-CD8STK-TM-A, having the sequence shown as SEQ ID No. 2 in that document. The CD86 protein is CD86-CD8TM, having the sequence shown above as SEQ ID No. 15.

Figure 2:
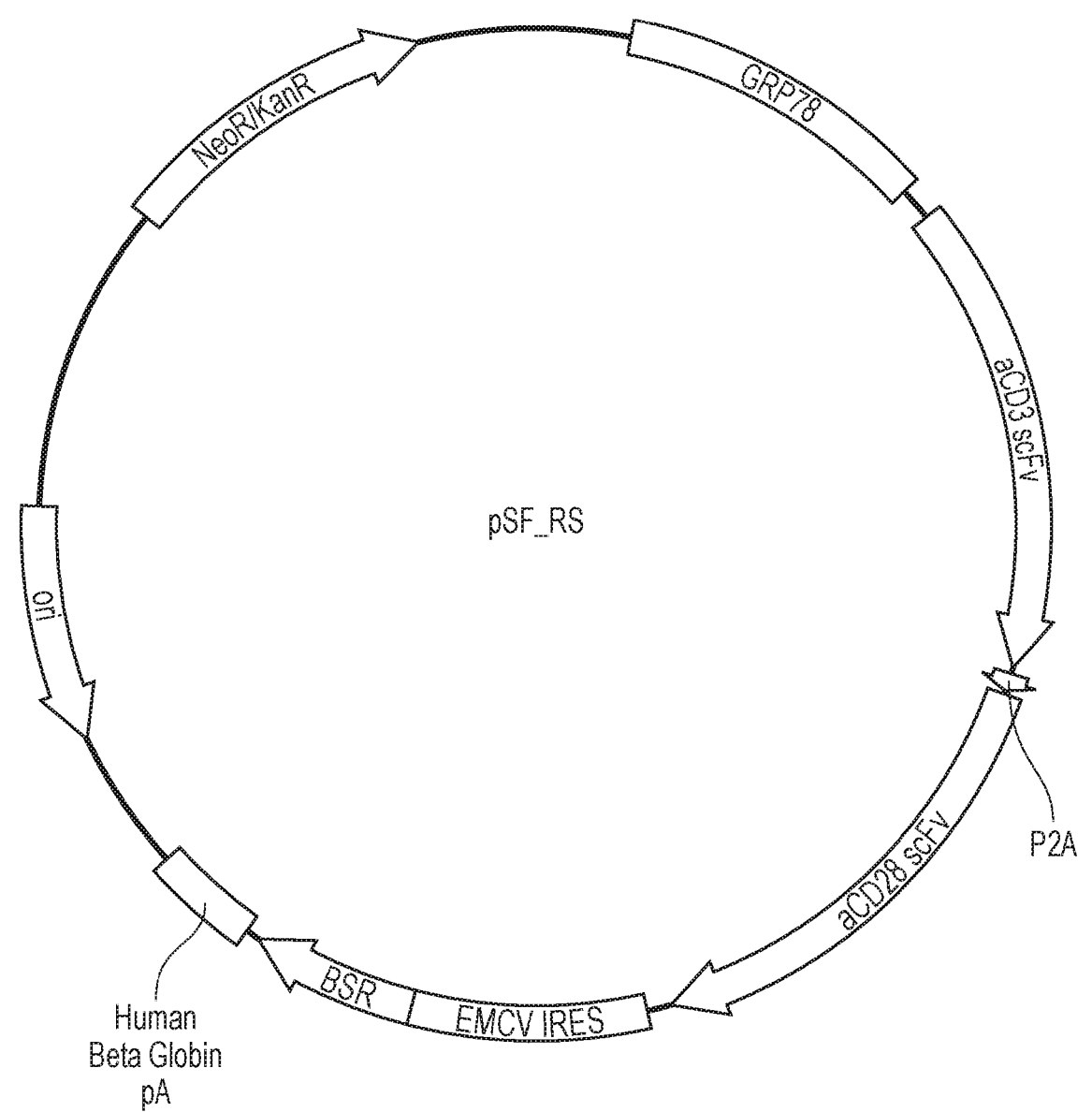
FIG. 2—Schematic diagram illustrating a plasmid used to produce VLPs expressing a CD3-binding transmembrane protein and a CD28-binding transmembrane protein ("RetroSTIM").

The plasmid encoding a CD3-binding transmembrane protein and a CD28-binding transmembrane protein is illustrated schematically in FIG. 2.

Transfections were performed using PEI Pro transfection reagent. 16 hours following transfection the medium was replaced with TexMacs culture medium supplemented with 3% human serum. 24 hours later the media was harvested and processed by Tangential Flow Filtration (TFF), to concentrate the VLP containing media and remove impurities.

Example 2—T-Cell Activation Using the VLPs

T-cells were activated with either TransAct or VLPs (4e4 VLPs per cell) were added to the culture medium, in addition to IL-7 and IL-15 (each 10 ng/ml). Cells were then cultured for up to seven days prior to analysis.

Figure 3:
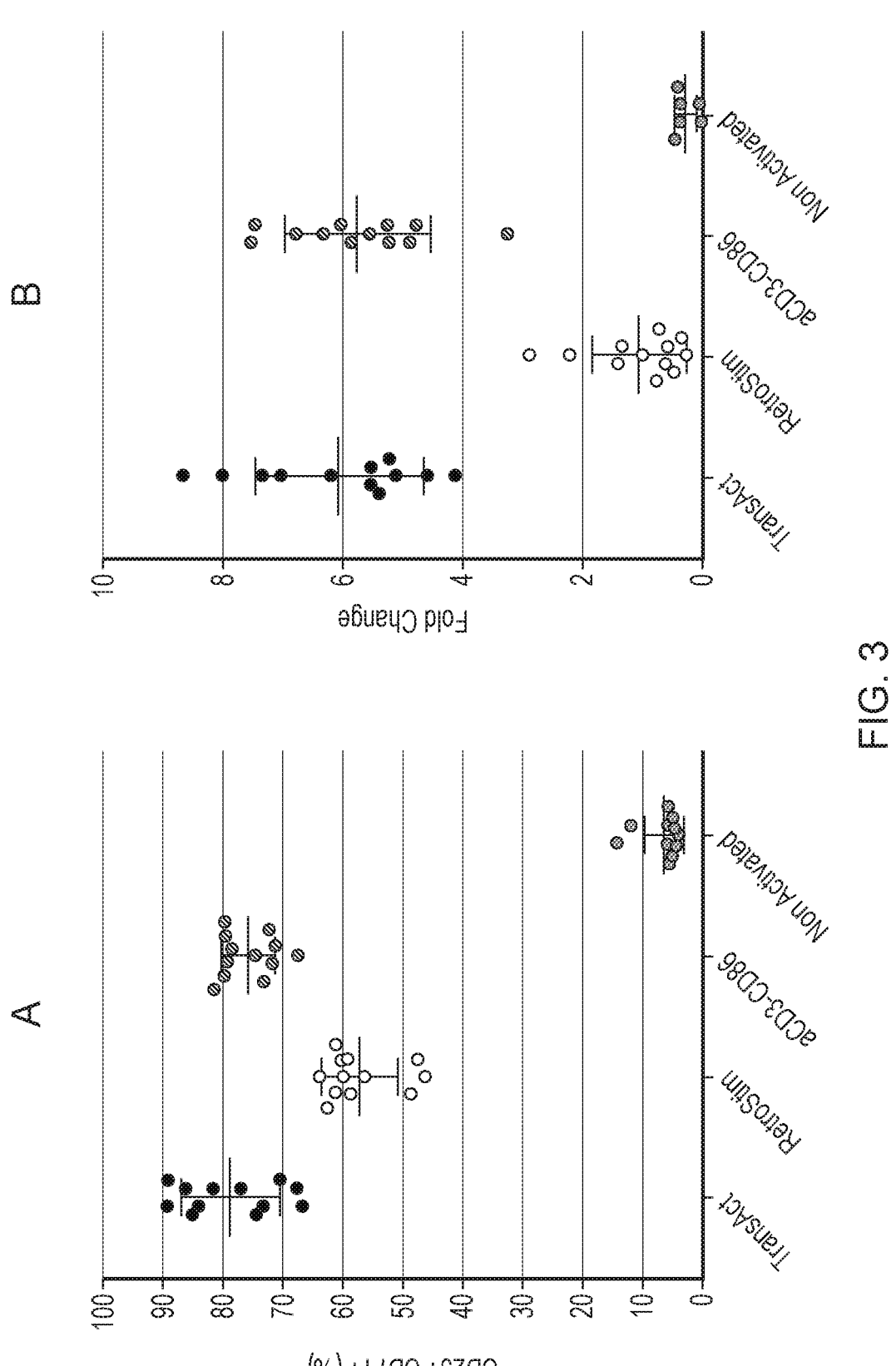
FIG. 3—Graphs comparing T cell activation by TransAct™; VLPs expressing a CD3-binding transmembrane protein and a CD28-binding transmembrane protein ("RetroSTIM"); VLPs expressing a CD3-binding transmembrane protein and a membrane protein comprising the extracellular domain of CD86 ("aCD3-CD86"). A: Activation; B: Expansion FIG. 4—Graph showing the results of a flow cytometry assay investigating T cells subsets in a T-cell composition following 7 days activation with TransAct™; VLPs expressing a CD3-binding transmembrane protein and a CD28-binding transmembrane protein ("RetroSTIM"); VLPs expressing a CD3-binding transmembrane protein and a membrane protein comprising the extracellular domain of CD86 ("aCD3-CD86").

For the analysis of activation phenotype, cells were analysed for the expression of CD25 and CD71 by flow cytometry on Day 2. The results are shown in FIG. 3A. T cells activated with aCD3-CD86 VLPs showed a higher level of activation than T cells activated with aCD3-aCD28. The level of activation achieved using aCD3-CD86 VLPs was comparable to TransAct.

To compare expansion between T cells activated by different means, the fold-change of T cells was analysed by flow cytometry. Fold expansion was determined by counting the cells on Day 7 and dividing by the starting number of cells (300,000). Fold expansion was calculated between Day 2 (Day of Transduction) and Day 7. The results are shown in FIG. 3B. T cells activated with aCD3-CD86 VLPs showed a higher level of expansion than T cells activated with aCD3-aCD28. The level of expansion achieved using aCD3-CD86 VLPs was comparable to TransAct.

Figures 4, 5:
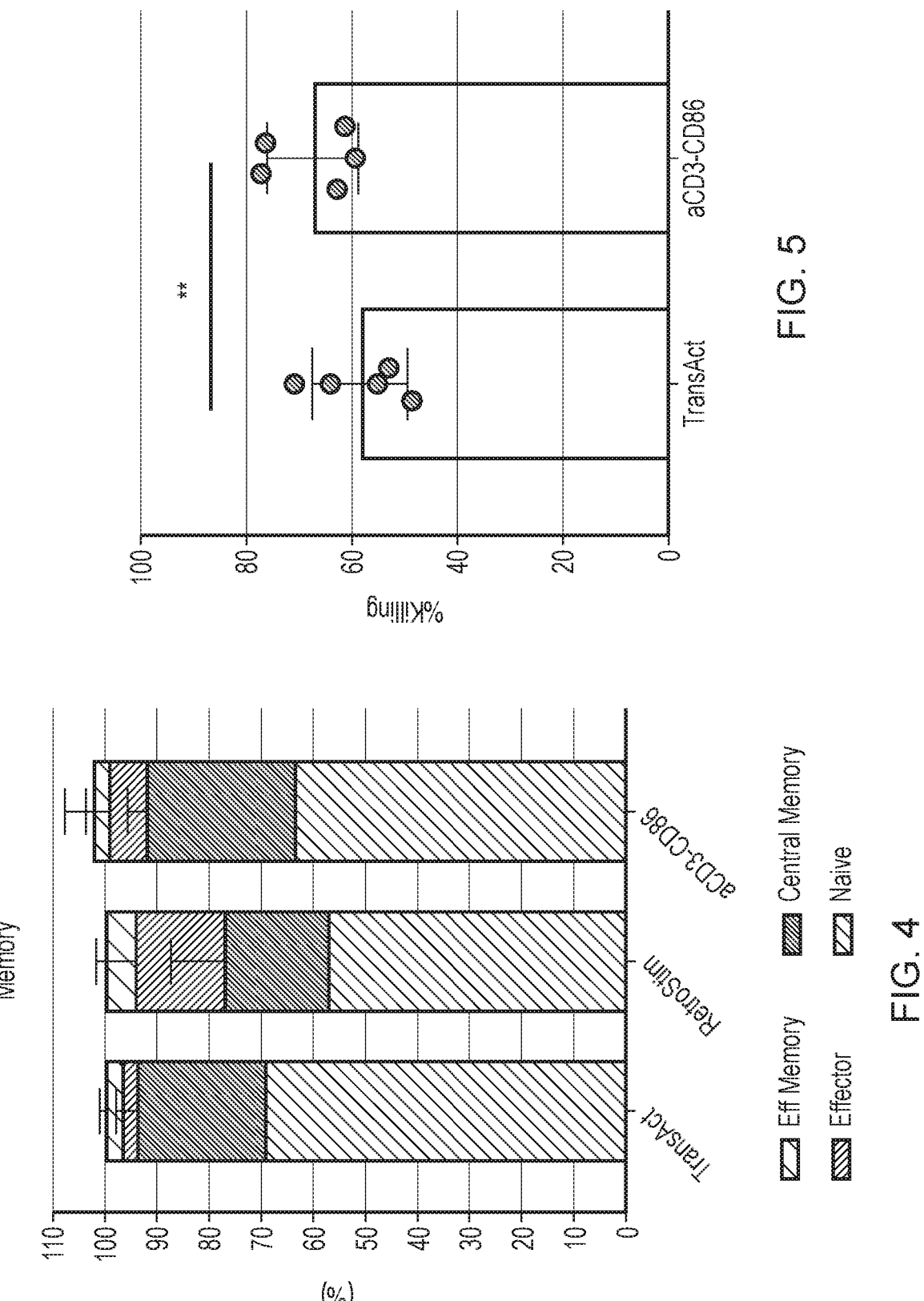
FIG. 5—Graph showing cytotoxicity following co-culture with target cells of T cells following activation with TransAct™; or VLPs expressing a CD3-binding transmembrane protein and a membrane protein comprising the extracellular domain of CD86 ("aCD3-CD86").

For analysis of T-cell phenotype, cells were analysed by flow cytometry on Day 7. The results are shown in FIG. 4. T cells activated with aCD3-CD86 VLPs showed a greater proportion of naïve and central memory cells than T cells activated with aCD3-aCD28.

Example 3—Cytotoxicity Assays with VLP-Activated CAR-T Cells

Following activation by the method described in Example 2, T cells were then cultured for a further 48 hours and transduced with a viral vector expressing a CD19 CAR and a CD22 CAR. This OR gate is described in WO2016/102965.

Transduced T-cells were co-cultured with Raji target cells at a ratio of 1:4, target:effector cells. Cytotoxicity was assessed by determining the number of target cells remaining following 48 hours of co-culture.

The results are shown in FIG. 5. CAR-T cells activated with aCD3-CD86 VLPs showed enhanced killing of target cells than CAR-T cells activated with TransAct.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

The invention claimed is:

1. A virus-like particle (VLP) having a viral envelope which comprises:

(i) a membrane protein comprising the extracellular domain of CD86 and the transmembrane domain of CD8, wherein the membrane protein comprises an amino acid sequence according to SEQ ID NO: 15; and (ii) a CD3-binding transmembrane protein.

2. The VLP according to claim 1, which is a retroviral-derived or lentiviral-derived VLP.

3. The VLP according to claim 1, which is derived from Moloney murine leukemia virus (Mo-MLV).

4. The VLP according to claim 1, wherein the CD3-binding transmembrane protein comprises an OKT3-derived antigen binding domain.

5. A nucleic acid construct which comprises a first nucleic acid sequence encoding a membrane protein comprising the extracellular domain of CD86 and the transmembrane domain of CD8, wherein the membrane protein comprises an amino acid sequence according to SEQ ID NO: 15; and a second nucleic acid sequence encoding a CD3-binding transmembrane protein.

6. A vector comprising a nucleic acid construct according to claim 5.

7. A kit of vectors which comprises:

(i) a first vector which comprises a nucleic acid sequence encoding a membrane protein comprising the extracellular domain of CD86 and the transmembrane domain of CD8, wherein the membrane protein comprises an amino acid sequence according to SEQ ID NO: 15; and (ii) a second vector which comprises a nucleic acid sequence encoding a CD3-binding transmembrane protein.

8. A method for activating a T cell which comprises the step of culturing the T cell in the presence of a VLP according to claim 1.

9. A method according to claim 8, wherein the T cell is also cultured in the presence of IL-7 or IL-15.

* * * * *

```
                          SEQUENCE LISTING

<160> NUMBER OF SEQ ID NOS: 17

<210> SEQ ID NO 1
<211> LENGTH: 7
<212> TYPE: PRT
<213> ORGANISM: Artificial Sequence
<220> FEATURE:
<223> OTHER INFORMATION: complementarity-determining region (CDR) of
      OKT3 antibody, CDRH1

<400> SEQUENCE: 1

Gly Tyr Thr Phe Thr Arg Tyr
1               5

<210> SEQ ID NO 2
<211> LENGTH: 6
<212> TYPE: PRT
<213> ORGANISM: Artificial Sequence
<220> FEATURE:
<223> OTHER INFORMATION: CDR of OKT3 antibody, CDRH2

<400> SEQUENCE: 2

Asn Pro Ser Arg Gly Tyr
1               5

<210> SEQ ID NO 3
<211> LENGTH: 10
<212> TYPE: PRT
<213> ORGANISM: Artificial Sequence
<220> FEATURE:
<223> OTHER INFORMATION: CDR of OKT3 antibody, CDRH3

<400> SEQUENCE: 3

Tyr Tyr Asp Asp His Tyr Cys Leu Asp Tyr
1               5                   10

<210> SEQ ID NO 4
<211> LENGTH: 10
<212> TYPE: PRT
<213> ORGANISM: Artificial Sequence
<220> FEATURE:
<223> OTHER INFORMATION: CDR of OKT3 antibody, CDRL1

<400> SEQUENCE: 4

Ser Ala Ser Ser Ser Val Ser Tyr Met Asn
```

```
1               5               10

<210> SEQ ID NO 5
<211> LENGTH: 7
<212> TYPE: PRT
<213> ORGANISM: Artificial Sequence
<220> FEATURE:
<223> OTHER INFORMATION: CDR of OKT3 antibody, CDRL2

<400> SEQUENCE: 5

Asp Thr Ser Lys Leu Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: CDR of OKT3 antibody, CDRL3

<400> SEQUENCE: 6

Gln Gln Trp Ser Ser Asn Pro Phe Thr
1               5

<210> SEQ ID NO 7
<211> LENGTH: 265
<212> TYPE: PRT
<213> ORGANISM: Artificial Sequence
<220> FEATURE:
<223> OTHER INFORMATION: scFv of OKT3 antibody

<400> SEQUENCE: 7

Met Glu Thr Asp Thr Leu Leu Leu Trp Val Leu Leu Leu Trp Val Pro
1               5               10              15

Gly Ser Thr Gly Gln Val Gln Leu Gln Gln Ser Gly Ala Glu Leu Ala
            20              25              30

Arg Pro Gly Ala Ser Val Lys Met Ser Cys Lys Ala Ser Gly Tyr Thr
        35              40              45

Phe Thr Arg Tyr Thr Met His Trp Val Lys Gln Arg Pro Gly Gln Gly
    50              55              60

Leu Glu Trp Ile Gly Tyr Ile Asn Pro Ser Arg Gly Tyr Thr Asn Tyr
65              70              75              80

Asn Gln Lys Phe Lys Asp Lys Ala Thr Leu Thr Thr Asp Lys Ser Ser
                85              90              95

Ser Thr Ala Tyr Met Gln Leu Ser Ser Leu Thr Ser Glu Asp Ser Ala
            100             105             110

Val Tyr Tyr Cys Ala Arg Tyr Tyr Asp Asp His Tyr Cys Leu Asp Tyr
        115             120             125

Trp Gly Gln Gly Thr Thr Leu Thr Val Ser Ser Ser Gly Gly Gly Gly
    130             135             140

Ser Gly Gly Gly Gly Ser Gly Gly Gly Gly Ser Gln Ile Val Leu Thr
145             150             155             160

Gln Ser Pro Ala Ile Met Ser Ala Ser Pro Gly Glu Lys Val Thr Met
                165             170             175

Thr Cys Ser Ala Ser Ser Ser Val Ser Tyr Met Asn Trp Tyr Gln Gln
            180             185             190

Lys Ser Gly Thr Ser Pro Lys Arg Trp Ile Tyr Asp Thr Ser Lys Leu
        195             200             205

Ala Ser Gly Val Pro Ala His Phe Arg Gly Ser Gly Ser Gly Thr Ser
    210             215             220
```

-continued

Tyr Ser Leu Thr Ile Ser Gly Met Glu Ala Glu Asp Ala Ala Thr Tyr
225                 230                 235                 240

Tyr Cys Gln Gln Trp Ser Ser Asn Pro Phe Thr Phe Gly Ser Gly Thr
                    245                 250                 255

Lys Leu Glu Ile Asn Arg Ser Asp Pro
            260                 265

<210> SEQ ID NO 8
<211> LENGTH: 246
<212> TYPE: PRT
<213> ORGANISM: Artificial Sequence
<220> FEATURE:
<223> OTHER INFORMATION: extracellular domain of human CD86

<400> SEQUENCE: 8

Asp Pro Gln Cys Thr Met Gly Leu Ser Asn Ile Leu Phe Val Met Ala
1               5                   10                  15

Phe Leu Leu Ser Gly Ala Ala Pro Leu Lys Ile Gln Ala Tyr Phe Asn
                20                  25                  30

Glu Thr Ala Asp Leu Pro Cys Gln Phe Ala Asn Ser Gln Asn Gln Ser
            35                  40                  45

Leu Ser Glu Leu Val Val Phe Trp Gln Asp Gln Glu Asn Leu Val Leu
        50                  55                  60

Asn Glu Val Tyr Leu Gly Lys Glu Lys Phe Asp Ser Val His Ser Lys
65                  70                  75                  80

Tyr Met Gly Arg Thr Ser Phe Asp Ser Asp Ser Trp Thr Leu Arg Leu
                85                  90                  95

His Asn Leu Gln Ile Lys Asp Lys Gly Leu Tyr Gln Cys Ile Ile His
            100                 105                 110

His Lys Lys Pro Thr Gly Met Ile Arg Ile His Gln Met Asn Ser Glu
            115                 120                 125

Leu Ser Val Leu Ala Asn Phe Ser Gln Pro Glu Ile Val Pro Ile Ser
        130                 135                 140

Asn Ile Thr Glu Asn Val Tyr Ile Asn Leu Thr Cys Ser Ser Ile His
145                 150                 155                 160

Gly Tyr Pro Glu Pro Lys Lys Met Ser Val Leu Leu Arg Thr Lys Asn
                165                 170                 175

Ser Thr Ile Glu Tyr Asp Gly Val Met Gln Lys Ser Gln Asp Asn Val
            180                 185                 190

Thr Glu Leu Tyr Asp Val Ser Ile Ser Leu Ser Val Ser Phe Pro Asp
            195                 200                 205

Val Thr Ser Asn Met Thr Ile Phe Cys Ile Leu Glu Thr Asp Lys Thr
        210                 215                 220

Arg Leu Leu Ser Ser Pro Phe Ser Ile Glu Leu Glu Asp Pro Gln Pro
225                 230                 235                 240

Pro Pro Asp His Ile Pro
                245

<210> SEQ ID NO 9
<211> LENGTH: 234
<212> TYPE: PRT
<213> ORGANISM: Artificial Sequence
<220> FEATURE:
<223> OTHER INFORMATION: spacer sequence, hinge-CH2CH3 of human IgG1

<400> SEQUENCE: 9

Ala Glu Pro Lys Ser Pro Asp Lys Thr His Thr Cys Pro Pro Cys Pro

-continued

```
1                5                  10                 15

Ala Pro Pro Val Ala Gly Pro Ser Val Phe Leu Phe Pro Pro Lys Pro
            20                 25                 30

Lys Asp Thr Leu Met Ile Ala Arg Thr Pro Glu Val Thr Cys Val Val
            35                 40                 45

Val Asp Val Ser His Glu Asp Pro Glu Val Lys Phe Asn Trp Tyr Val
        50                 55                 60

Asp Gly Val Glu Val His Asn Ala Lys Thr Lys Pro Arg Glu Glu Gln
65                 70                 75                 80

Tyr Asn Ser Thr Tyr Arg Val Val Ser Val Leu Thr Val Leu His Gln
                85                 90                 95

Asp Trp Leu Asn Gly Lys Glu Tyr Lys Cys Lys Val Ser Asn Lys Ala
            100                105                110

Leu Pro Ala Pro Ile Glu Lys Thr Ile Ser Lys Ala Lys Gly Gln Pro
            115                120                125

Arg Glu Pro Gln Val Tyr Thr Leu Pro Pro Ser Arg Asp Glu Leu Thr
            130                135                140

Lys Asn Gln Val Ser Leu Thr Cys Leu Val Lys Gly Phe Tyr Pro Ser
145                150                155                160

Asp Ile Ala Val Glu Trp Glu Ser Asn Gly Gln Pro Glu Asn Asn Tyr
                165                170                175

Lys Thr Thr Pro Pro Val Leu Asp Ser Asp Gly Ser Phe Phe Leu Tyr
            180                185                190

Ser Lys Leu Thr Val Asp Lys Ser Arg Trp Gln Gln Gly Asn Val Phe
            195                200                205

Ser Cys Ser Val Met His Glu Ala Leu His Asn His Tyr Thr Gln Lys
        210                215                220

Ser Leu Ser Leu Ser Pro Gly Lys Lys Asp
225                230
```

```
<210> SEQ ID NO 10
<211> LENGTH: 46
<212> TYPE: PRT
<213> ORGANISM: Artificial Sequence
<220> FEATURE:
<223> OTHER INFORMATION: spacer sequence, human CD8 stalk

<400> SEQUENCE: 10

Thr Thr Thr Pro Ala Pro Arg Pro Pro Thr Pro Ala Pro Thr Ile Ala
1                5                  10                 15

Ser Gln Pro Leu Ser Leu Arg Pro Glu Ala Cys Arg Pro Ala Ala Gly
            20                 25                 30

Gly Ala Val His Thr Arg Gly Leu Asp Phe Ala Cys Asp Ile
            35                 40                 45
```

```
<210> SEQ ID NO 11
<211> LENGTH: 20
<212> TYPE: PRT
<213> ORGANISM: Artificial Sequence
<220> FEATURE:
<223> OTHER INFORMATION: spacer sequence, human IgG1 hinge

<400> SEQUENCE: 11

Ala Glu Pro Lys Ser Pro Asp Lys Thr His Thr Cys Pro Pro Cys Pro
1                5                  10                 15

Lys Asp Pro Lys
            20
```

-continued

```
<210> SEQ ID NO 12
<211> LENGTH: 185
<212> TYPE: PRT
<213> ORGANISM: Artificial Sequence
<220> FEATURE:
<223> OTHER INFORMATION: spacer sequence, CD2 ectodomain

<400> SEQUENCE: 12

Lys Glu Ile Thr Asn Ala Leu Glu Thr Trp Gly Ala Leu Gly Gln Asp
1               5                   10                  15

Ile Asn Leu Asp Ile Pro Ser Phe Gln Met Ser Asp Asp Ile Asp Asp
            20                  25                  30

Ile Lys Trp Glu Lys Thr Ser Asp Lys Lys Lys Ile Ala Gln Phe Arg
        35                  40                  45

Lys Glu Lys Glu Thr Phe Lys Glu Lys Asp Thr Tyr Lys Leu Phe Lys
    50                  55                  60

Asn Gly Thr Leu Lys Ile Lys His Leu Lys Thr Asp Asp Gln Asp Ile
65                  70                  75                  80

Tyr Lys Val Ser Ile Tyr Asp Thr Lys Gly Lys Asn Val Leu Glu Lys
                85                  90                  95

Ile Phe Asp Leu Lys Ile Gln Glu Arg Val Ser Lys Pro Lys Ile Ser
            100                 105                 110

Trp Thr Cys Ile Asn Thr Thr Leu Thr Cys Glu Val Met Asn Gly Thr
            115                 120                 125

Asp Pro Glu Leu Asn Leu Tyr Gln Asp Gly Lys His Leu Lys Leu Ser
        130                 135                 140

Gln Arg Val Ile Thr His Lys Trp Thr Thr Ser Leu Ser Ala Lys Phe
145                 150                 155                 160

Lys Cys Thr Ala Gly Asn Lys Val Ser Lys Glu Ser Ser Val Glu Pro
                165                 170                 175

Val Ser Cys Pro Glu Lys Gly Leu Asp
            180                 185

<210> SEQ ID NO 13
<211> LENGTH: 259
<212> TYPE: PRT
<213> ORGANISM: Artificial Sequence
<220> FEATURE:
<223> OTHER INFORMATION: spacer sequence, CD34 ectodomain

<400> SEQUENCE: 13

Ser Leu Asp Asn Asn Gly Thr Ala Thr Pro Glu Leu Pro Thr Gln Gly
1               5                   10                  15

Thr Phe Ser Asn Val Ser Thr Asn Val Ser Tyr Gln Glu Thr Thr Thr
            20                  25                  30

Pro Ser Thr Leu Gly Ser Thr Ser Leu His Pro Val Ser Gln His Gly
        35                  40                  45

Asn Glu Ala Thr Thr Asn Ile Thr Glu Thr Thr Val Lys Phe Thr Ser
    50                  55                  60

Thr Ser Val Ile Thr Ser Val Tyr Gly Asn Thr Asn Ser Ser Val Gln
65                  70                  75                  80

Ser Gln Thr Ser Val Ile Ser Thr Val Phe Thr Thr Pro Ala Asn Val
                85                  90                  95

Ser Thr Pro Glu Thr Thr Leu Lys Pro Ser Leu Ser Pro Gly Asn Val
            100                 105                 110

Ser Asp Leu Ser Thr Thr Ser Thr Ser Leu Ala Thr Ser Pro Thr Lys
            115                 120                 125
```

-continued

```
Pro Tyr Thr Ser Ser Ser Pro Ile Leu Ser Asp Ile Lys Ala Glu Ile
    130             135             140

Lys Cys Ser Gly Ile Arg Glu Val Lys Leu Thr Gln Gly Ile Cys Leu
145             150             155             160

Glu Gln Asn Lys Thr Ser Ser Cys Ala Glu Phe Lys Lys Asp Arg Gly
                165             170             175

Glu Gly Leu Ala Arg Val Leu Cys Gly Glu Glu Gln Ala Asp Ala Asp
            180             185             190

Ala Gly Ala Gln Val Cys Ser Leu Leu Leu Ala Gln Ser Glu Val Arg
            195             200             205

Pro Gln Cys Leu Leu Leu Val Leu Ala Asn Arg Thr Glu Ile Ser Ser
    210             215             220

Lys Leu Gln Leu Met Lys Lys His Gln Ser Asp Leu Lys Lys Leu Gly
225             230             235             240

Ile Leu Asp Phe Thr Glu Gln Asp Val Ala Ser His Gln Ser Tyr Ser
            245             250             255

Gln Lys Thr
```

```
<210> SEQ ID NO 14
<211> LENGTH: 350
<212> TYPE: PRT
<213> ORGANISM: Artificial Sequence
<220> FEATURE:
<223> OTHER INFORMATION: CD3-binding membrane protein, OKT3-CD8STK-TM-A

<400> SEQUENCE: 14
```

```
Met Glu Thr Asp Thr Leu Leu Leu Trp Val Leu Leu Leu Trp Val Pro
1               5               10              15

Gly Ser Thr Gly Gln Val Gln Leu Gln Gln Ser Gly Ala Glu Leu Ala
            20              25              30

Arg Pro Gly Ala Ser Val Lys Met Ser Cys Lys Ala Ser Gly Tyr Thr
        35              40              45

Phe Thr Arg Tyr Thr Met His Trp Val Lys Gln Arg Pro Gly Gln Gly
    50              55              60

Leu Glu Trp Ile Gly Tyr Ile Asn Pro Ser Arg Gly Tyr Thr Asn Tyr
65              70              75              80

Asn Gln Lys Phe Lys Asp Lys Ala Thr Leu Thr Thr Asp Lys Ser Ser
            85              90              95

Ser Thr Ala Tyr Met Gln Leu Ser Ser Leu Thr Ser Glu Asp Ser Ala
            100             105             110

Val Tyr Tyr Cys Ala Arg Tyr Tyr Asp Asp His Tyr Cys Leu Asp Tyr
            115             120             125

Trp Gly Gln Gly Thr Thr Leu Thr Val Ser Ser Ser Gly Gly Gly Gly
    130             135             140

Ser Gly Gly Gly Gly Ser Gly Gly Gly Gly Ser Gln Ile Val Leu Thr
145             150             155             160

Gln Ser Pro Ala Ile Met Ser Ala Ser Pro Gly Glu Lys Val Thr Met
            165             170             175

Thr Cys Ser Ala Ser Ser Ser Val Ser Tyr Met Asn Trp Tyr Gln Gln
            180             185             190

Lys Ser Gly Thr Ser Pro Lys Arg Trp Ile Tyr Asp Thr Ser Lys Leu
        195             200             205

Ala Ser Gly Val Pro Ala His Phe Arg Gly Ser Gly Ser Gly Thr Ser
    210             215             220
```

```
Tyr Ser Leu Thr Ile Ser Gly Met Glu Ala Glu Asp Ala Ala Thr Tyr
225             230             235             240

Tyr Cys Gln Gln Trp Ser Ser Asn Pro Phe Thr Phe Gly Ser Gly Thr
            245             250             255

Lys Leu Glu Ile Asn Arg Ser Asp Pro Thr Thr Thr Pro Ala Pro Arg
            260             265             270

Pro Pro Thr Pro Ala Pro Thr Ile Ala Ser Gln Pro Leu Ser Leu Arg
        275             280             285

Pro Glu Ala Cys Arg Pro Ala Ala Gly Gly Ala Val His Thr Arg Gly
        290             295             300

Leu Asp Phe Ala Cys Asp Ile Tyr Ile Trp Ala Pro Leu Ala Gly Thr
305             310             315             320

Cys Gly Val Leu Leu Leu Ser Leu Val Ile Thr Leu Tyr Cys Asn His
            325             330             335

Arg Asn Arg Arg Arg Val Cys Lys Cys Pro Arg Pro Val Val
            340             345             350

<210> SEQ ID NO 15
<211> LENGTH: 307
<212> TYPE: PRT
<213> ORGANISM: Artificial Sequence
<220> FEATURE:
<223> OTHER INFORMATION: membrane protein, CD86-CD8TM

<400> SEQUENCE: 15

Asp Pro Gln Cys Thr Met Gly Leu Ser Asn Ile Leu Phe Val Met Ala
1               5               10              15

Phe Leu Leu Ser Gly Ala Ala Pro Leu Lys Ile Gln Ala Tyr Phe Asn
            20              25              30

Glu Thr Ala Asp Leu Pro Cys Gln Phe Ala Asn Ser Gln Asn Gln Ser
            35              40              45

Leu Ser Glu Leu Val Val Phe Trp Gln Asp Gln Glu Asn Leu Val Leu
        50              55              60

Asn Glu Val Tyr Leu Gly Lys Glu Lys Phe Asp Ser Val His Ser Lys
65              70              75              80

Tyr Met Gly Arg Thr Ser Phe Asp Ser Asp Ser Trp Thr Leu Arg Leu
            85              90              95

His Asn Leu Gln Ile Lys Asp Lys Gly Leu Tyr Gln Cys Ile Ile His
            100             105             110

His Lys Lys Pro Thr Gly Met Ile Arg Ile His Gln Met Asn Ser Glu
        115             120             125

Leu Ser Val Leu Ala Asn Phe Ser Gln Pro Glu Ile Val Pro Ile Ser
        130             135             140

Asn Ile Thr Glu Asn Val Tyr Ile Asn Leu Thr Cys Ser Ser Ile His
145             150             155             160

Gly Tyr Pro Glu Pro Lys Lys Met Ser Val Leu Leu Arg Thr Lys Asn
            165             170             175

Ser Thr Ile Glu Tyr Asp Gly Val Met Gln Lys Ser Gln Asp Asn Val
            180             185             190

Thr Glu Leu Tyr Asp Val Ser Ile Ser Leu Ser Val Ser Phe Pro Asp
        195             200             205

Val Thr Ser Asn Met Thr Ile Phe Cys Ile Leu Glu Thr Asp Lys Thr
        210             215             220

Arg Leu Leu Ser Ser Pro Phe Ser Ile Glu Leu Glu Asp Pro Gln Pro
225             230             235             240
```

```
Pro Pro Asp His Ile Pro Ile Tyr Ile Trp Ala Pro Leu Ala Gly Thr
            245         250             255

Cys Gly Val Leu Leu Leu Ser Leu Val Ile Thr Leu Tyr Cys Asn His
            260         265             270

Arg Asn Arg Arg Arg Val Cys Lys Cys Pro Arg Pro Val Val Asn Ala
        275         280             285

Tyr Val Ala Thr Ala Asp Met Tyr Arg Ala Arg Ala Gly Ser Ile Pro
    290             295             300

Pro Pro Pro
305

<210> SEQ ID NO 16
<211> LENGTH: 20
<212> TYPE: PRT
<213> ORGANISM: Artificial Sequence
<220> FEATURE:
<223> OTHER INFORMATION: self-cleaving peptide sequence

<400> SEQUENCE: 16

Arg Ala Glu Gly Arg Gly Ser Leu Leu Thr Cys Gly Asp Val Glu Glu
1               5               10              15

Asn Pro Gly Pro
            20

<210> SEQ ID NO 17
<211> LENGTH: 20
<212> TYPE: PRT
<213> ORGANISM: Artificial Sequence
<220> FEATURE:
<223> OTHER INFORMATION: self-cleaving peptide sequence

<400> SEQUENCE: 17

Gln Cys Thr Asn Tyr Ala Leu Leu Lys Leu Ala Gly Asp Val Glu Ser
1               5               10              15

Asn Pro Gly Pro
            20
```